US00RE36011E

United States Patent [19]

Grushka et al.

[11] E Patent Number: Re. 36,011

[45] Reissued Date of Patent: Dec. 29, 1998

[54] PROTEIN SEPARATIONS BY CAPILLARY ELECTROPHORESIS USING AMINO ACID-CONTAINING BUFFERS

[75] Inventors: Eli Grushka, D.N. Tzfon Yehuda, Israel; Cheng-Ming Liu, Yorba Linda, Calif.

[73] Assignee: Bio-Rad Laboratories, Inc., Hercules, Calif.

[21] Appl. No.: 975,179

[22] Filed: Nov. 20, 1997

Related U.S. Patent Documents

Reissue of:

[64] Patent No.: 5,660,701
Issued: Aug. 26, 1997
Appl. No.: 610,105
Filed: Feb. 29, 1996

[51] Int. Cl.[6] ..... G01N 27/26; G01N 27/447

[52] U.S. Cl. ..... 204/451; 204/601

[58] Field of Search ..... 204/451, 452, 204/453, 454, 455, 601, 602, 603, 604, 605

[56] References Cited

U.S. PATENT DOCUMENTS 5,221,447 6/1993 Hjerten ..... 204/454 X

OTHER PUBLICATIONS

Nava Cohen and Eli Grushka, "Controlling electroosmotic flow in capillary zone electrophoresis" Journal of Chromatography A, 678 (1994) 167–175.

Lei Wang et al, "Study on the reproducibility of migration time from dipeptides in high performance capillary electrophoresis" SEPU, 11(4) (1993) 207–209.

*Primary Examiner*—Robert J. Warden
*Assistant Examiner*—John S. Starsiak, Jr.
*Attorney, Agent, or Firm*—Townsend and Townsend and Crew LLP

[57] ABSTRACT

Protein mixtures are separated by capillary electrophoresis in a buffer containing one or more amino acids in an amount sufficient to prevent or substantially reduce the degree of protein binding to the wall of the capillary.

18 Claims, 12 Drawing Sheets

PROTEIN SEPARATIONS BY CAPILLARY ELECTROPHORESIS USING AMINO ACID-CONTAINING BUFFERS

Matter enclosed in heavy brackets [ ] appears in the original patent but forms no part of this reissue specification; matter printed in italics indicates the additions made by reissue.

This invention resides in the field of electrophoresis of proteins, and addresses methods for achieving high resolution in protein separations by capillary electrophoresis.

BACKGROUND OF THE INVENTION

Analyses of the levels of proteins in mammalian serum are widely used as indications of various diseases and abnormal physiological conditions. A subnormal level of albumin, for example, is an indication of renal disease, while high albumin is a characteristic of dehydration. Similarly, an elevated level of pre-β lipoprotein can be an indication of chronic alcoholism or of hyperestrogenism, and elevated levels of β-lipoprotein can be indicative of high cholesterol.

Proteins are readily separated by electrophoresis, and both slab gel electrophoresis and capillary electrophoresis have been used. The advantage of capillary electrophoresis is that very small samples can be analyzed, and because of the high wall surface-to-volume ratio in a capillary the heat generated by the electric current is rapidly dissipated, which permits separations to be peformed at high voltages and therefore shorter separation times. Open capillary zone electrophoresis, in which the separation medium is a buffer solution, is particularly useful since the capillary can be easily conditioned and filled with the solution for each use.

The electrokinetic potential at the capillary wall surface is a prominent factor in the movement and separation of the proteins upon imposition of the electric field. This movement and separation can be changed by the interactions between the proteins and the capillary wall. Separations run at high or low pH, which place a net charge on the proteins, may minimize the interaction between the proteins and the capillary wall. These interactions are particularly strong in capillaries made of fused silica, causing adsorption of the proteins at the capillary wall. The adsorption has an influence on the electroosmotic flow by changing the charge density of the wall surface. Changes in the electroosmotic flow in turn cause changes in migration times, peak resolution and reproducibility. These considerations also apply, although often to a lesser extent, in slab electrophoresis, particularly with the use of thin slabs.

Efforts to improve the separation by suppressing the interaction between the proteins and the capillary wall or other wall enclosing the separation zone have resulted in the development of a variety of treatments, additives and operating conditions. One technique is to use a buffer having a pH that is higher than the isoelectric points of the sample proteins, thereby imparting a net negative charge to the proteins to repel them from the negatively charged wall. A disadvantage of this method is the risk of hydrolysis and other structural changes in the proteins. Strongly basic buffers with high salt concentrations have also been used as a means of blocking ionic interactions between the proteins and the wall. High salt concentrations however increase the conductivity of the buffer and hence the rate of heat generation inside the capillary. A further alternative has been to coat the wall to mask or neutralize the potential, and coatings for this purpose have included polyacrylamide, glycol, and pentafluorobenzoyl groups. Disadvantages of coated walls include low reproducibility due to the gradual deterioration of the coating over repeated use, and a reduction in the speed of the analysis due to the elimination of the electroendosmotic flow component. A still further alternative has been the inclusion of borate ion in the running buffer to form complexes with the the sugar moieties of glycoproteins and thereby neutralize their charge. The use of borate ion entails a risk of denaturing certain proteins, particularly immunoglobulins, and thereby creating a separate peak. Also, borate ion increases the conductivity of the buffer, limiting the electric field and the speed with which the separation can be achieved.

SUMMARY OF THE INVENTION

It has now been discovered that effective and rapid protein separations can be achieved by capillary electrophoresis without the detrimental characteristics of protein-wall interactions, by using an alkaline run buffer containing an amino acid. Such a buffer is useful in electrophoresis in general, including various electrophoretic cell geometries, but is of particular interest with electrophoresis performed in capillaries. Capillaries of silica-containing material, particularly fused silica whose internal surface has not been coated, are preferred.

In optimal usage, the amino acid-containing buffer is used in the pretreatment of the capillary or other electrophoretic cell prior to insertion of the sample, as a diluting buffer for the sample as it is inserted, and as the electrode buffers in each of the two electrode reservoirs which complete the electrical circuit between the voltage source and the separation region. The amino acids reduce both protein-wall interactions and protein-protein interactions, and avoid the risk of denaturation. Separations performed with buffers according to this invention will therefore provide the same or an equivalent separation as those achieved by slab gel electrophoresis, with high precision, high resolution and reproducibility.

These and other features and advantages of the invention will become more apparent from the description that follows.

DETAILED DESCRIPTION OF THE INVENTION AND PREFERRED EMBODIMENTS

Figure 1:
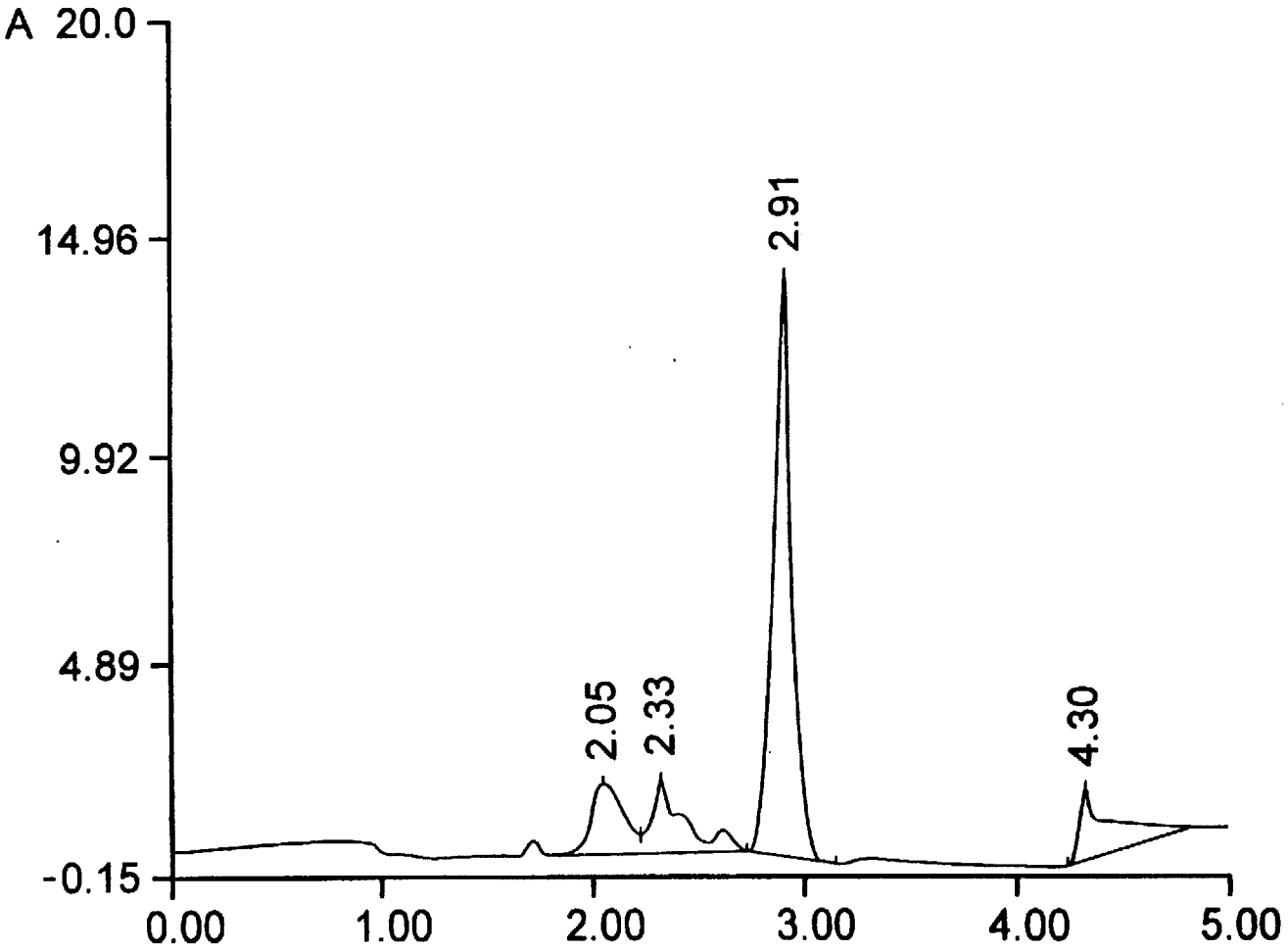
FIG. 1 is an electropherogram of a normal serum sample analyzed by capillary zone electrophoresis using a buffer of the present invention.

Amino acids are effective in this invention by virtue of their negative charge at high pH due to the ionization of the carboxyl group (—$COO^-$). Useful amino acids include both the essential and nonessential amino acids. Examples of some of the more prominent amino acids are glycine, alanine, valine, leucine, isoleucine, serine, threonine, proline, aspartate, glutamate, arginine, threonine and glutamine. Preferred among these are glycine, alanine, valine, leucine, isoleucine, serine, threonine and proline, with the more preferred being glycin, alanine, valine, leucine and isoleucine. A preferred class of amino acids are $\alpha$-amino acids, and particularly those that have a relatively low conductivity in aqueous solution, such as glycine. Two or more amino acids may be used in a single buffer solution rather than just one, although in most cases a single amino acid will suffice.

The concentration of the amino acid is not critical, and the optimal concentration in any particular case may vary depending on such factors as the dilution of the sample being analyzed and the nature of the capillary, both in terms of any surface treatments which may have been applied and its inner diameter. In general, best results are obtained with amino acid concentrations within the range of about 10 mM to about 500 mM, and preferably about 20 mM to about 200 mM.

The buffer is preferably an aqueous solution, although not necessarily limited to any particular solvent. The solution is alkine to impose a negative charge on the amino acid. While the degree of alkalinity may vary, preferred solutions are those with pH within the range of about 8 to about 11, and most preferably about 9 to about 10.

Samples to be analyzed by the method of this invention are preferably diluted with the buffer prior to being injected into or loaded on the column. The degree of dilution is not critical and may vary. Best results will generally be achieved, however, with dilutions of 1 part sample to a range of from about 1 part to about 100 parts of the buffer solution, and preferably 1 part sample to a range of from about 3 parts to about 30 parts of the buffer solution.

The invention has application to liquid samples of protein mixtures in general, with particular utility when used for the analysis of samples of biological fluids. Examples of such fluids are urine, saliva, cerebrospinal fluid, whole blood, plasma and serum. Serum samples are of particular interest.

The buffer solution may contain further additives. Salts, for example, may be included to increase the ionic strength of the solution for purposes of enhancing the resolution of the separated protein zones. Preferred salts are inorganic salts, such as halides of alkaline and alkaline earth metals. Examples are sodium and potassium halides, such as chloride, iodide, bromide and fluoride, with sodium chloride preferred. The concentration of the salt is not critical and can vary, with optimal ranges depending on the other variables of the system. A typical range is from about 1 mM to about 100 nM, and preferably from about 10 mM to about 30 mM.

It is also preferred that the buffer solution contain no other buffering agents than the amino acid. It is further preferred that the buffer solution contain no additives which form complexes or otherwise bind or interact with the proteins or the capillary wall. In particular, the buffer preferably does not include borate ion, phosphate ion, or substituted analogs of either borate or phosphate ion. Nevertheless, benefits of the invention can still be attained even if these additives are present.

The invention likewise offers benefits of improved performance in capillaries of a variety of materials, with or without coatings. As noted above, however, the invention is of particular interest in capillaries of silica-containing materials such as fused silica, glass or quartz, and most particularly silica-containing capillaries whose internal wall surfaces are uncoated.

Protein separations in accordance with the present invention are readily performed with equipment, materials, operating conditions and procedures used in conventional electrophoretic separations. Preferred capillaries are those having internal diameters of less than about 200 microns, and most preferably about 10 microns to about 100 microns. The invention is also applicable to electrophoretic separations performed in slab-shaped cells and other non-capillary systems. For capillary systems, voltages of at least about 50 volts per centimeter length of the capillary are preferred, with a voltage range of about 100 volts/cm to about 1000 volts/cm particularly preferred.

The following examples are offered strictly for purposes of illustration, and are intended neither to define nor to limit the invention in any manner.

EXAMPLE 1

A running buffer was prepared by dissolving 25 mM glycine and 25 mM NaCl in deionized water and adjusting the pH to 11 with 1N NaOH. A fused silica capillary measuring 50μ, inside diameter, with an outside diameter of 375μ and a 25 cm total length (20 cm from the inlet to the detector) was used. The inside surface of the capillary was uncoated, while the outside surface was coated with polyimide to improve flexibility and resist breakage. The capillary was preconditioned by washing for 2 minutes with 1N NaOH, rinsing for 2 minutes with distilled water, and washing for 5 minutes with the running buffer. The capillary was then conditioned by passing 20 kV through the capillary for 2 hours while filled with the running buffer.

Drug-free (normal) serum was diluted 50 times with the running buffer, then injected into the capillary by pressure at 2 psi (0.14 kg/cm$^2$) for 1 second. Electrophoresis was then run at a voltage of 15.00 kV with detection by absorptivity at a wavelength of 214 mm. Five peaks appeared within three minutes, as shown by the electropherogram in FIG. 1. The peaks represent, from left to right, the γ (gamma) globulin fraction, the β (beta) globulin fraction, the $\alpha_1$ (alpha-1) globulin fraction, the $\alpha_2$ (alpha-2) globulin fraction, and the albumin fraction. The peaks are well-defined with a steady baseline.

EXAMPLE 2

This example uses a buffer solution of the present invention to compare electropherograms of serum samples from human subjects with various diseases, and also includes electropherograms taken on agarose gels without the presence of amino add.

The amino acid running buffer was prepared by dissolving 11.26 g of glycine and 0.76 g NaCl in 800 mL distilled water, adjusting the pH of the solution to 9.6 with 1N NaOH, then bringing the final volume to 1000 mL with deionized water and passing the resulting solution through a 0.5μ filter. The resulting running buffer contained 150 mM glycine. The serum samples were prepared by mixing one part sample with nine parts running buffer (volume basis). The capillary was fused silica with an inside diameter of 25μ and an outside diameter of 360μ, with a length of 24 cm, of which 19 cm was the distance from inlet to detector. The interior surface of the capillary was uncoated, while the outer surface was coated with polyimide. The capillary was prepared by washing with 1N NaOH for 30 seconds, followed by a rinse of 30 seconds with the running buffer. Capillary zone electrophoresis (using the running buffer alone as the separation medium) was conducted at a temperature of 20° C., with a sample injection of 5 psi (0.35 kg/cm$^2$) for one second, and a run voltage of 15 kV at 16 μAmpere for three minutes, and detection at 214 nm.

The comparison tests were performed in pre-cast agarose slab gels, using barbital buffer. The buffer composition was 10 mM 5,5-diethylbarbituric acid plus 50 mM 5,5-diethylbarbituric add sodium salt, with a pH of 8.6 and a voltage of 100 V, using blue stain to render the protein visible.

Figure 2A:
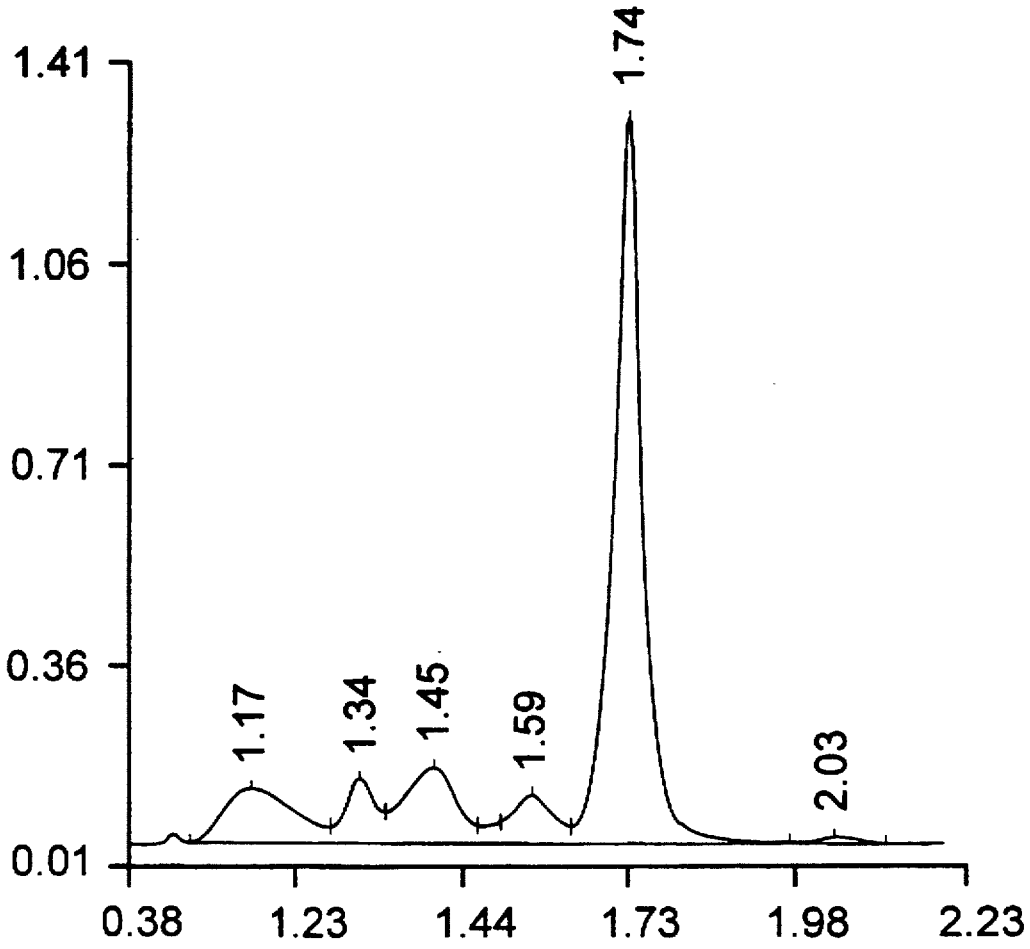
FIG. 2a is an electropherogram of a normal serum sample analyzed by capillary zone electrophoresis using a buffer of the present invention, using a different set of operating conditions from those of FIG. 1.
Figure 2B:
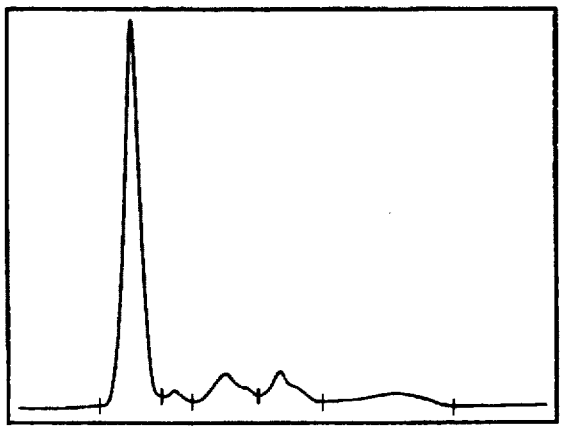
FIG. 2b is a densitometry scan of the same serum sample as FIG. 2a analyzed by slab gel electrophoresis using a buffer outside the scope of this invention.
Figure 3A:
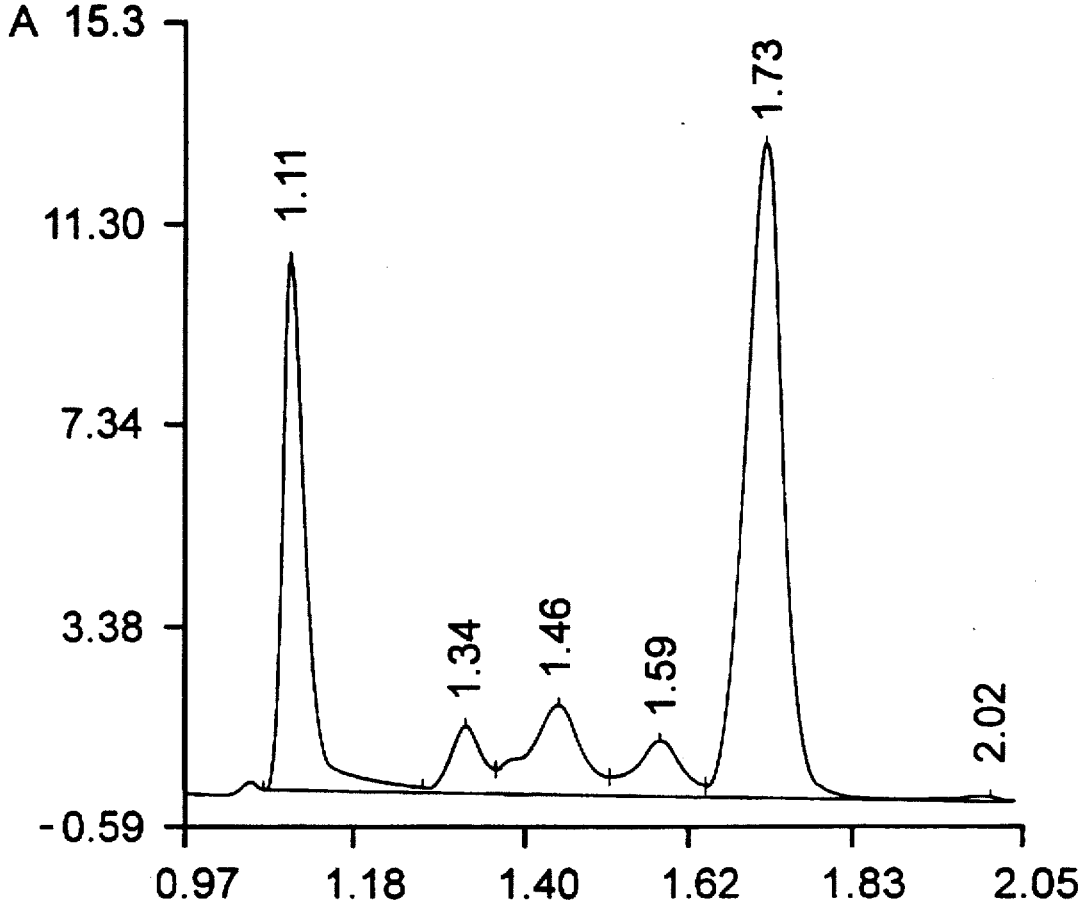
FIG. 3a is an electropherogram of a serum sample from a subject with monoclonal gammopathy, using capillary zone electrophoresis with a buffer of the present invention.
Figure 3B:
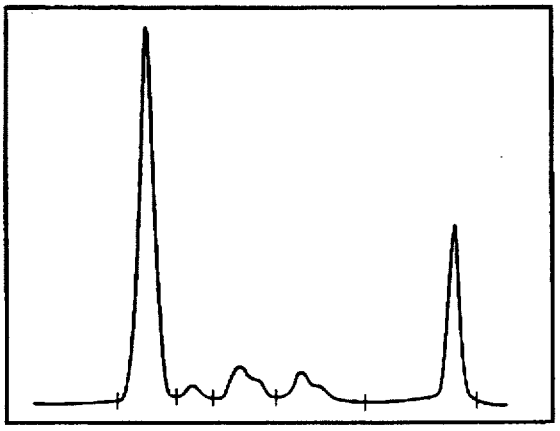
FIG. 3b is a densitometry scan of the same serum sample as FIG. 3a analyzed by slab gel electrophoresis using a buffer outside the scope of this invention.
Figure 4A:
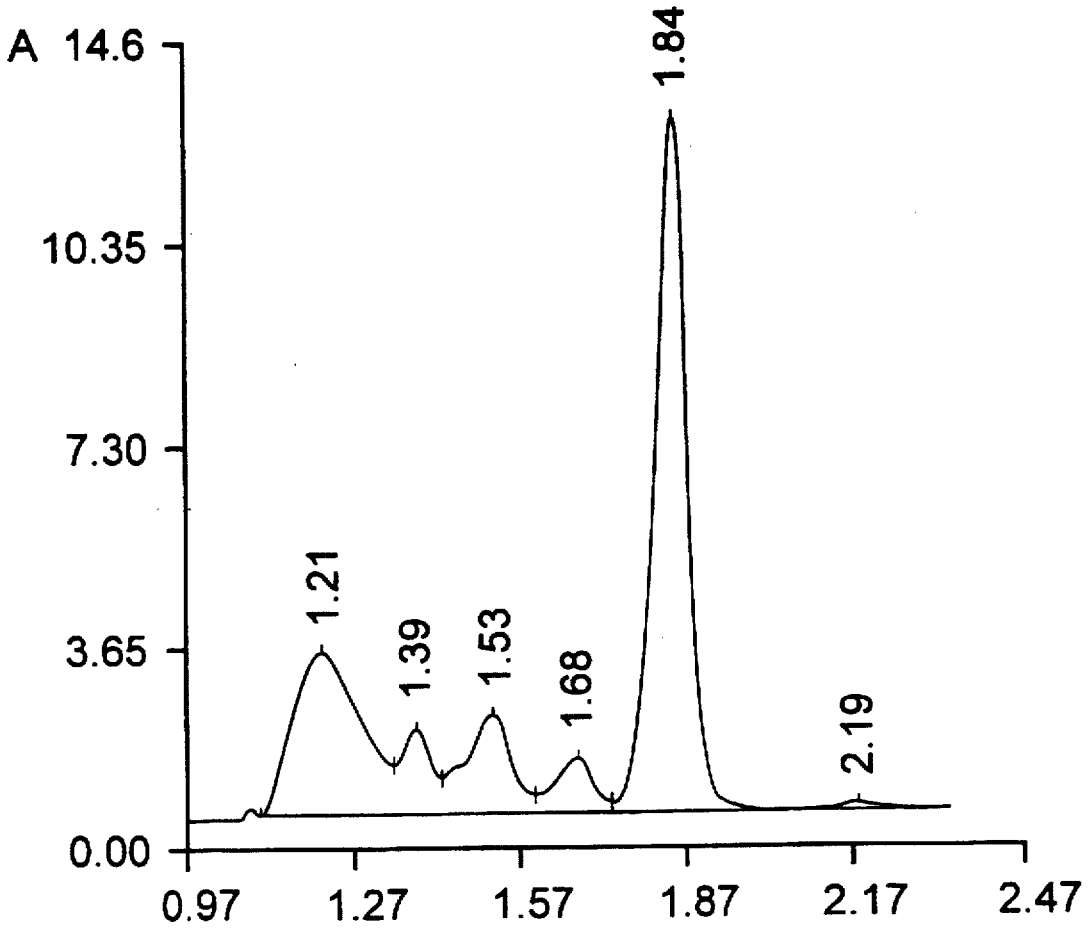
FIG. 4a is an electropherogram of a serum sample from a subject with polyclonal gammopathy, using capillary zone electrophoresis with a buffer of the present invention.
Figure 4B:
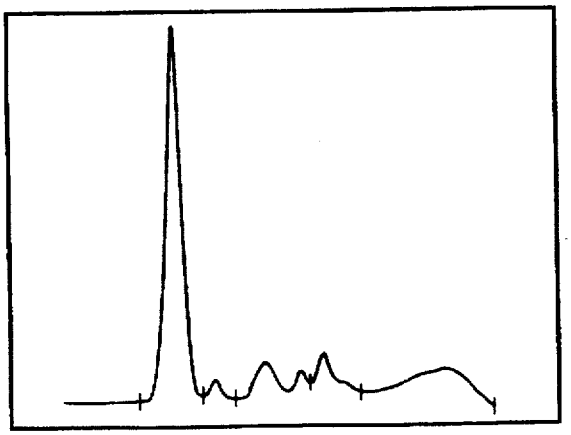
FIG. 4b is a densitometry scan of the same serum sample as FIG. 4a analyzed by slab gel electrophoresis using a buffer outside the scope of this invention.
Figure 5A:
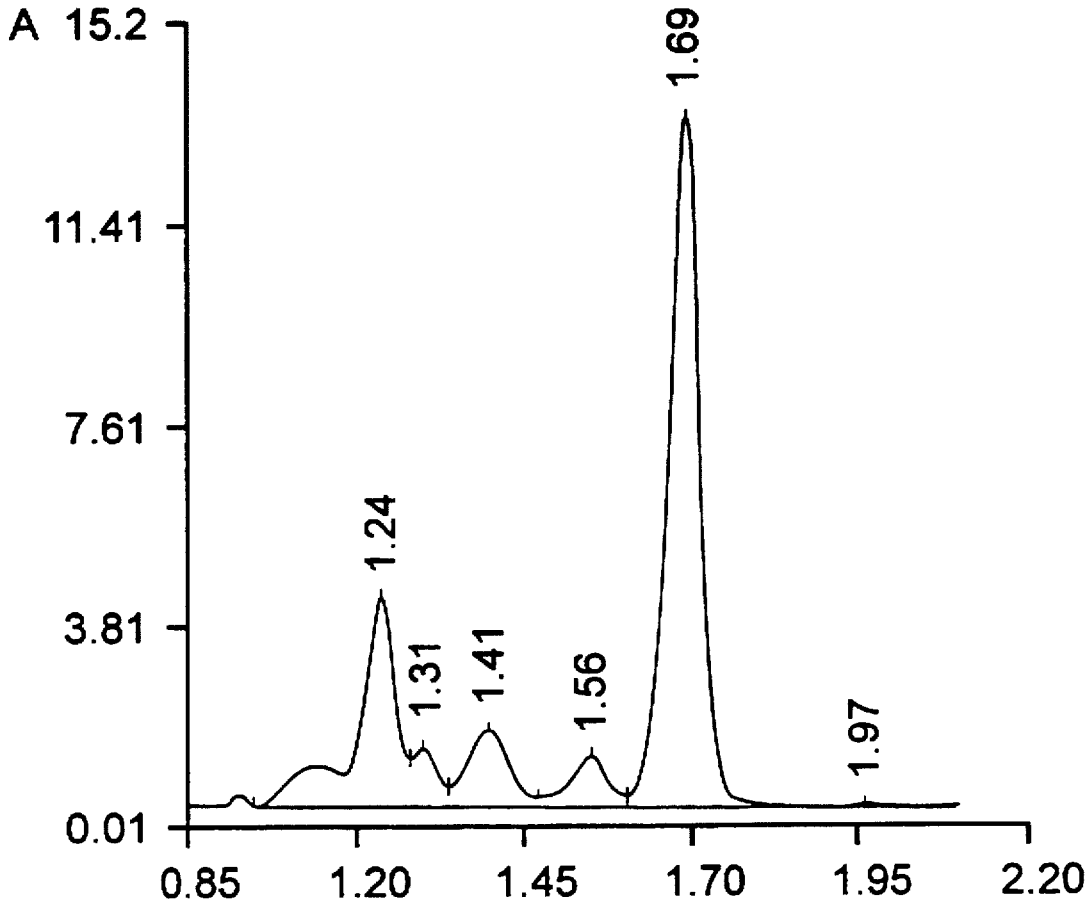
FIG. 5a is an electropherogram of a serum sample from a subject with IgA monoclonal gammopathy with normal IgG, using capillary zone electrophoresis with a buffer of the present invention.
Figure 5B:
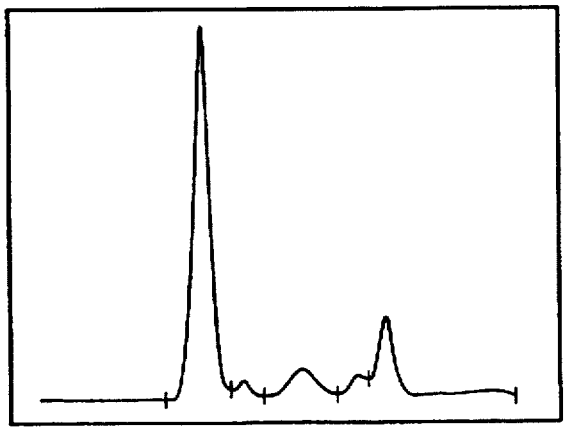
FIG. 5b is a densitometry scan of the same serum sample as FIG. 5a analyzed by slab gel electrophoresis using a buffer outside the scope of this invention.
Figure 6A:
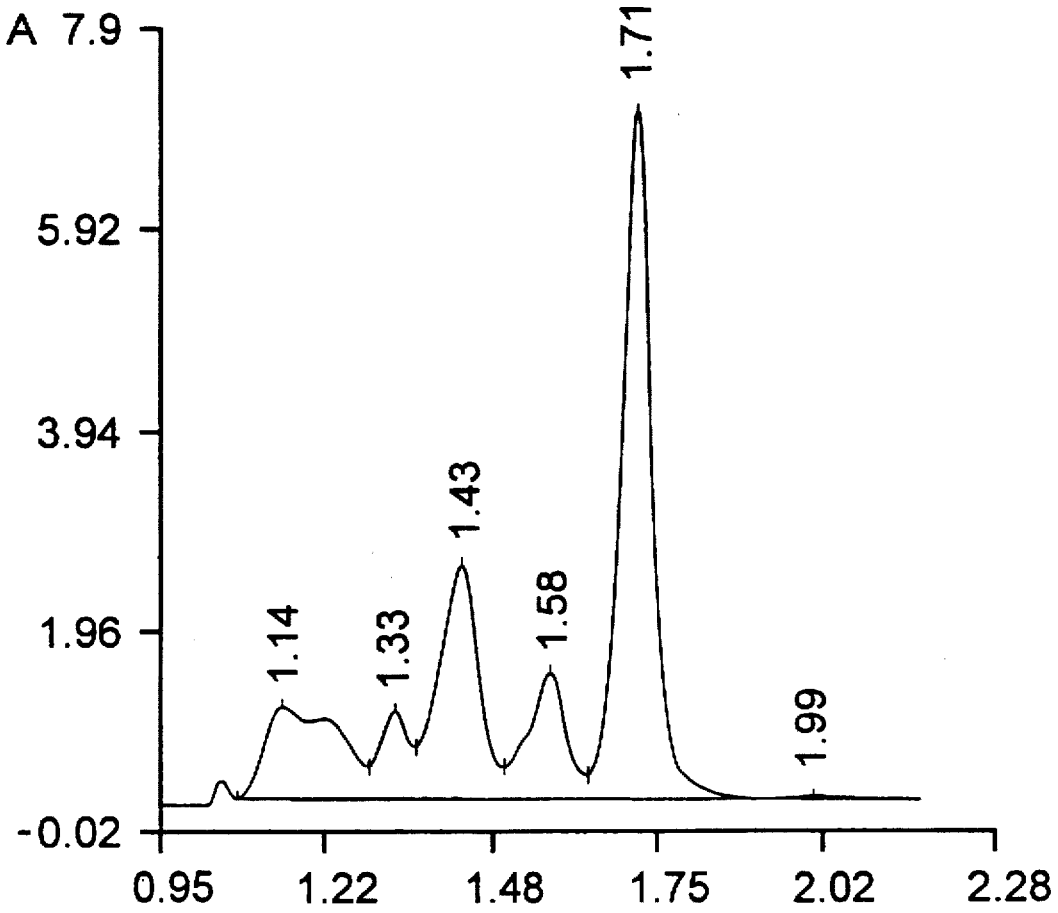
FIG. 6a is an electropherogram of a serum sample from a subject with biclonal or oligoclonal gammopathy with elevated $\alpha_1$ and $\alpha_2$, using capillary zone electrophoresis with a buffer of the present invention.
Figure 6B:
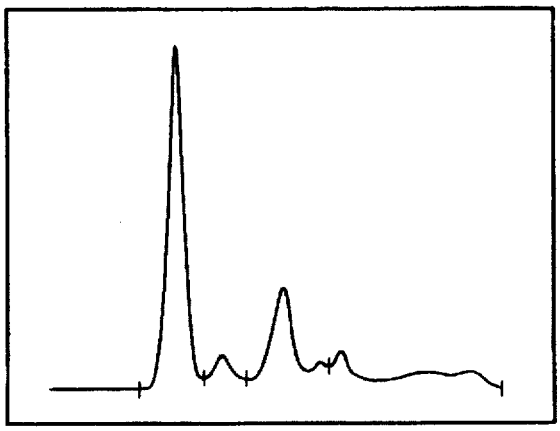
FIG. 6b is a densitometry scan of the same serum sample as FIG. 6a analyzed by slab gel electrophoresis using a buffer outside the scope of this invention.
Figure 7A:
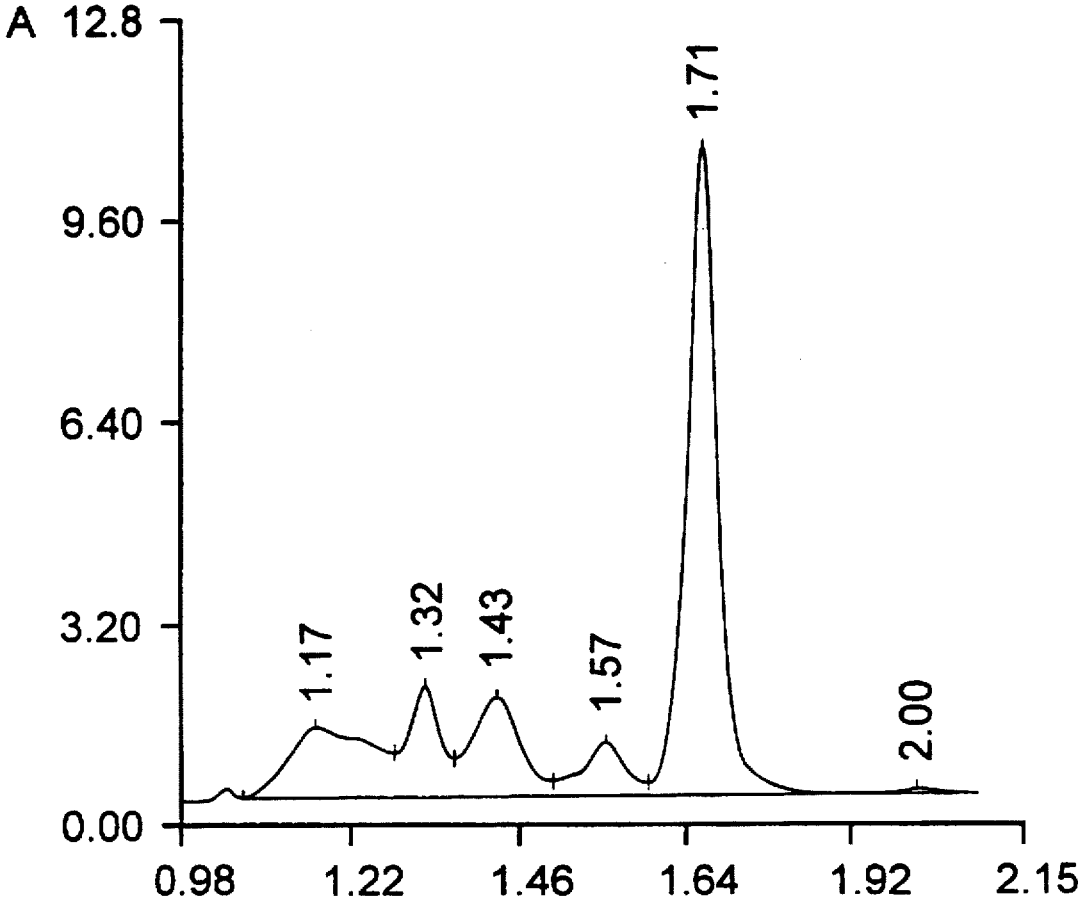
FIG. 7a is an electropherogram of a serum sample from a subject with minimonoclonal gammopathy, using capillary zone electrophoresis with a buffer of the present invention.
Figure 7B:
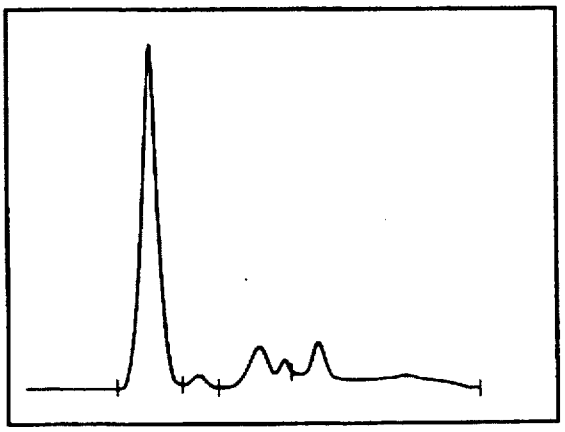
FIG. 7b is a densitometry scan of the same serum sample as FIG. 7a analyzed by slab gel electrophoresis using a buffer outside the scope of this invention.

The electropherogram traces are shown in individual figures as follows:

FIG. 2a: normal serum using capillary zone electrophoresis with glycine running buffer FIG. 2b: normal serum using agarose slab gel with barbital buffer FIG. 3a: serum from subject with monoclonal gammopathy, using capillary zone electrophoresis with glycine running buffer FIG. 3b: serum from subject with monoclonal gammopathy, using agarose slab gel with barbital buffer FIG. 4a: serum from subject with polyclonal gammopathy, using capillary zone electrophoresis with glycine running buffer FIG. 4b: serum from subject with polyclonal gammopathy, using agarose slab gel with barbital buffer FIG. 5a: serum from subject with IgA monoclonal gammopathy with normal IgG, using capillary zone electrophoresis with glycine running buffer FIG. 5b: serum from subject with IgA monoclonal gammopathy with normal IgG, using agarose slab gel with barbital buffer FIG. 6a: serum from subject with biclonal or oligoclonal gammopathy with elevated $\alpha_1$ and $\alpha_2$, using capillary zone electrophoresis with glycine running buffer FIG. 6b: serum from subject with biclonal or oligoclonal gammopathy with elevated $\alpha_1$ and $\alpha_2$, using agarose slab gel with barbital buffer FIG. 7a: serum from subject with minimonoclonal gammopathy, using capillary zone electrophoresis with glycine running buffer FIG. 7b: serum from subject with minimonoclonal gammopathy, using agarose slab gel with barbital buffer The peaks shown in all of these electropherograms, with the exception of FIGS. 5a and 5b, are albumin and the fractions $\alpha_1$, $\alpha_2$, β and γ, in that order, from right to left in the capillary zone electrophoresis traces, and from left to right in the slab gel electrophoresis traces, albumin being the largest peak in each case. In FIG. 5a, the two leftmost peaks (at retention times of 1.16 and 124, respectively) are IgG and IgA, respectively, as are the two rightmost peaks in FIG. 5b. The traces show that the peaks were separated as effectively in the capillary zone electrophoresis traces with the glycine buffer as they were in the slab gel electrophoresis traces with the barbital buffer.

EXAMPLE 3

This example reports a correlation study in which serum samples from 37 different patients were analyzed by the two methods described in Example 2. Comparisons of the areas under the peaks were made between the two methods for each of the five components, the areas having been determined by integrators. Regression analyses were also performed. The results are plotted in FIGS. 8a, 8b, 8c, 8d and 8e, for the albumin, $\alpha_1$, αand γ fractions, respectively.

Figure 8A:
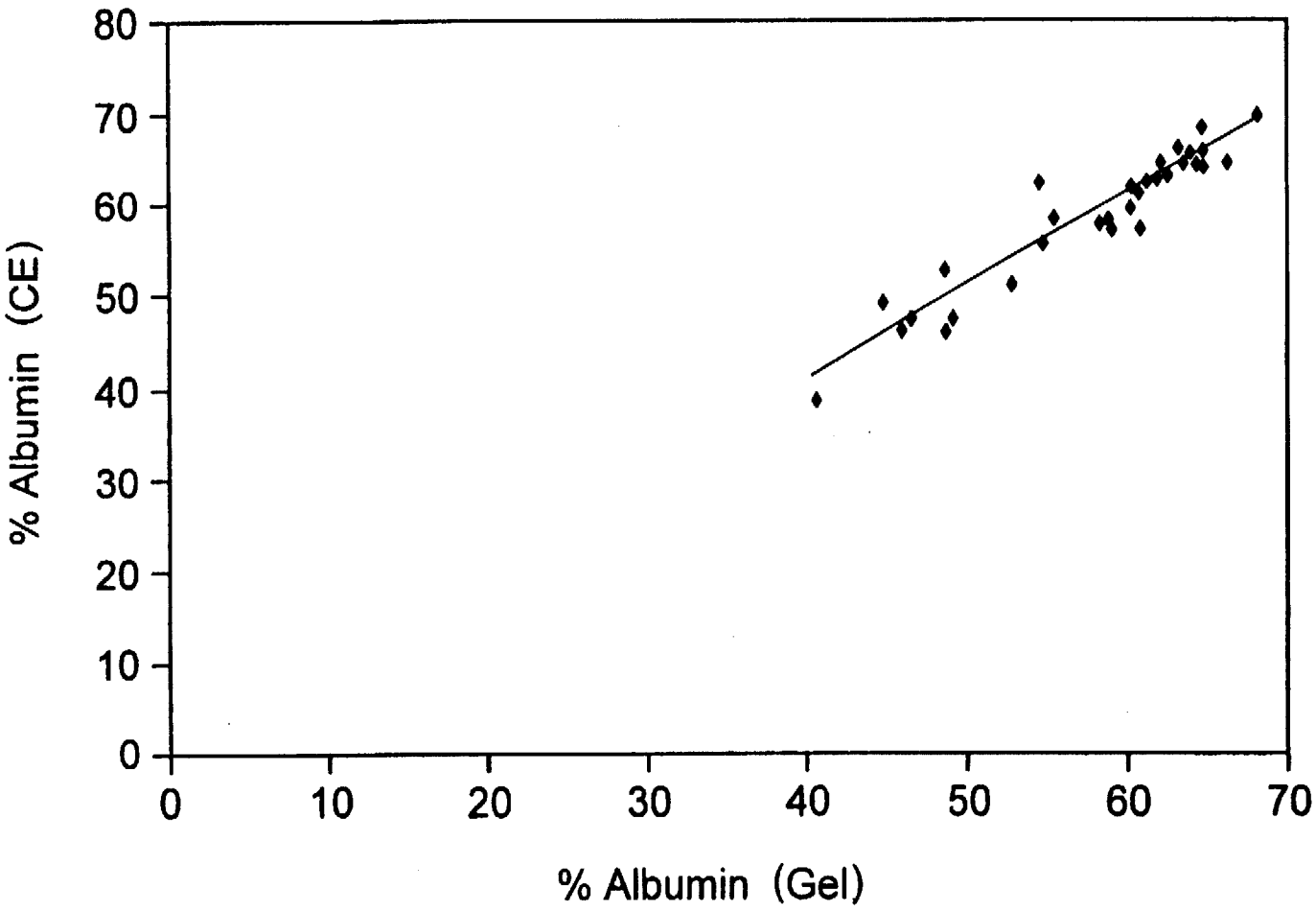
FIG. 8a is a correlation plot of albumin peak areas obtained by capillary zone electrophoresis with a buffer of the present invention and those obtained by slab gel electrophoresis using a buffer outside the scope of this invention.

The regression analyses produced the following:

FIG. 8a: $y=0.9836x+2.4469$; $R^2=0.9176$

Figure 8B:
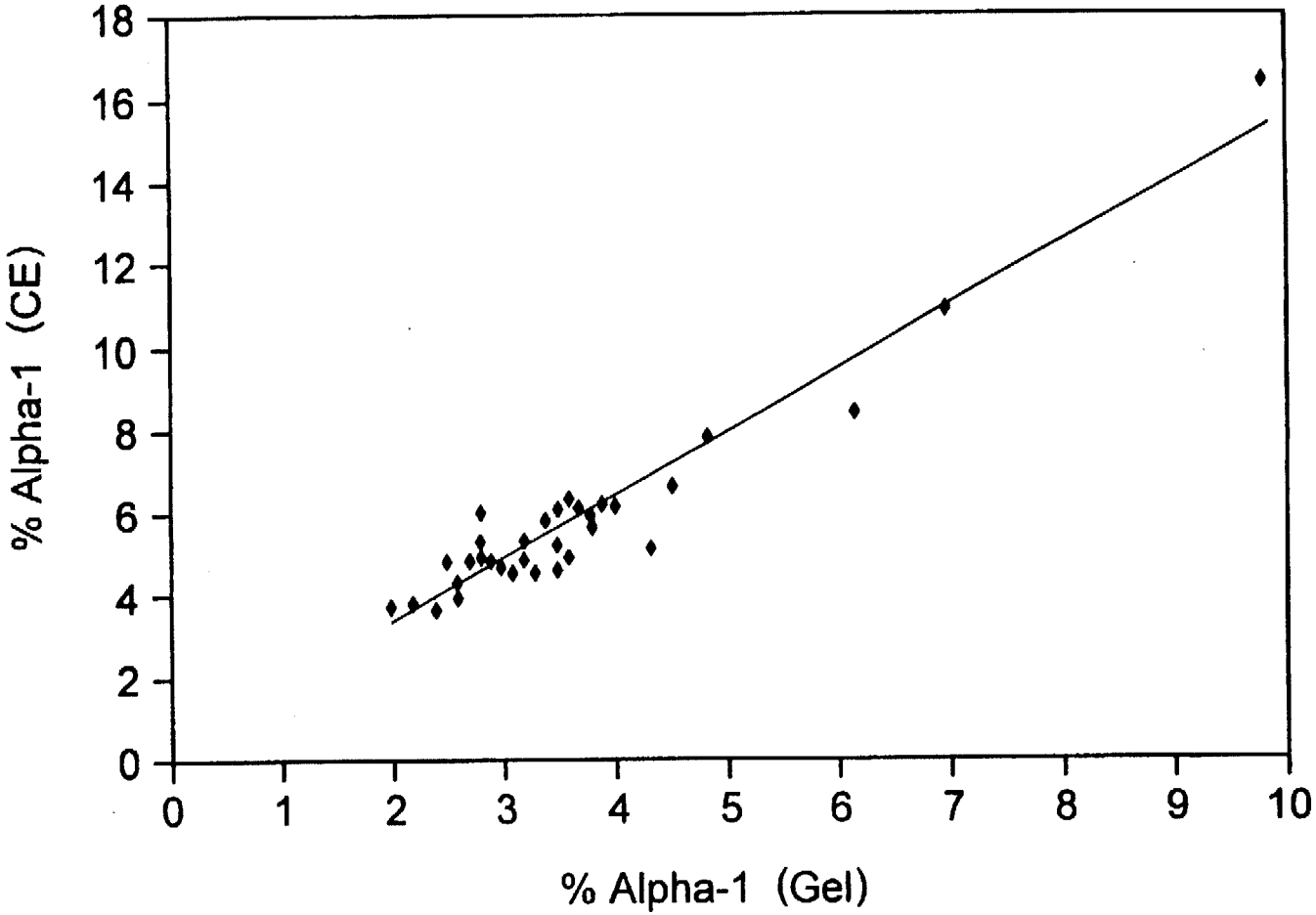
FIG. 8b is a correlation plot analogous to that of FIG. 8a for $\alpha_1$ globulin peak areas.

FIG. 8b: $y=1.5197x+0.2363$; $R^2=0.9223s$

Figure 8C:
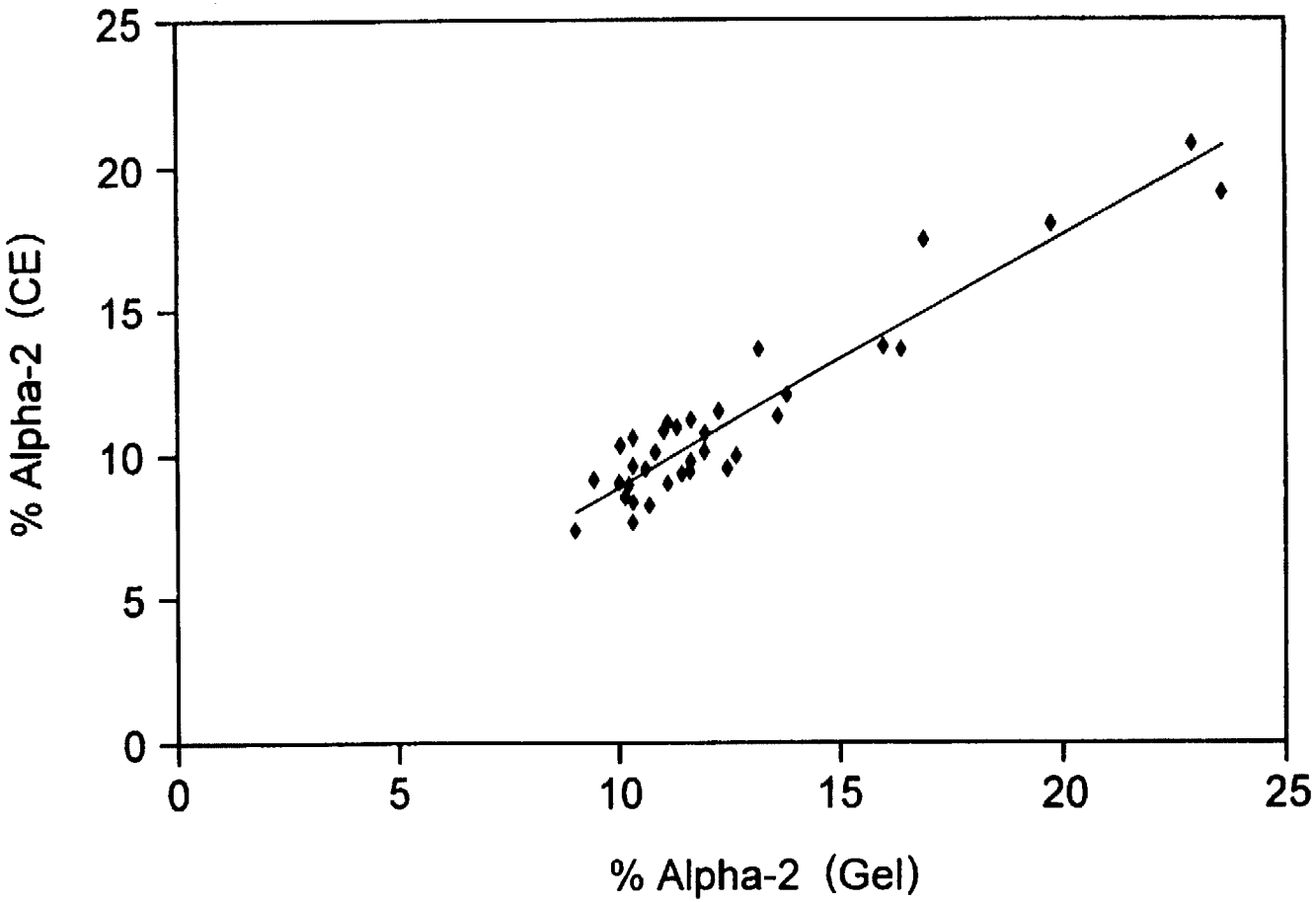
FIG. 8c is a comparison plot analogous to that of FIG. 8a for $\alpha_2$ globulin peak areas.

FIG. 8c: $y=0.8888x-0.0989$; $R^2=0.8931$

Figure 8D:
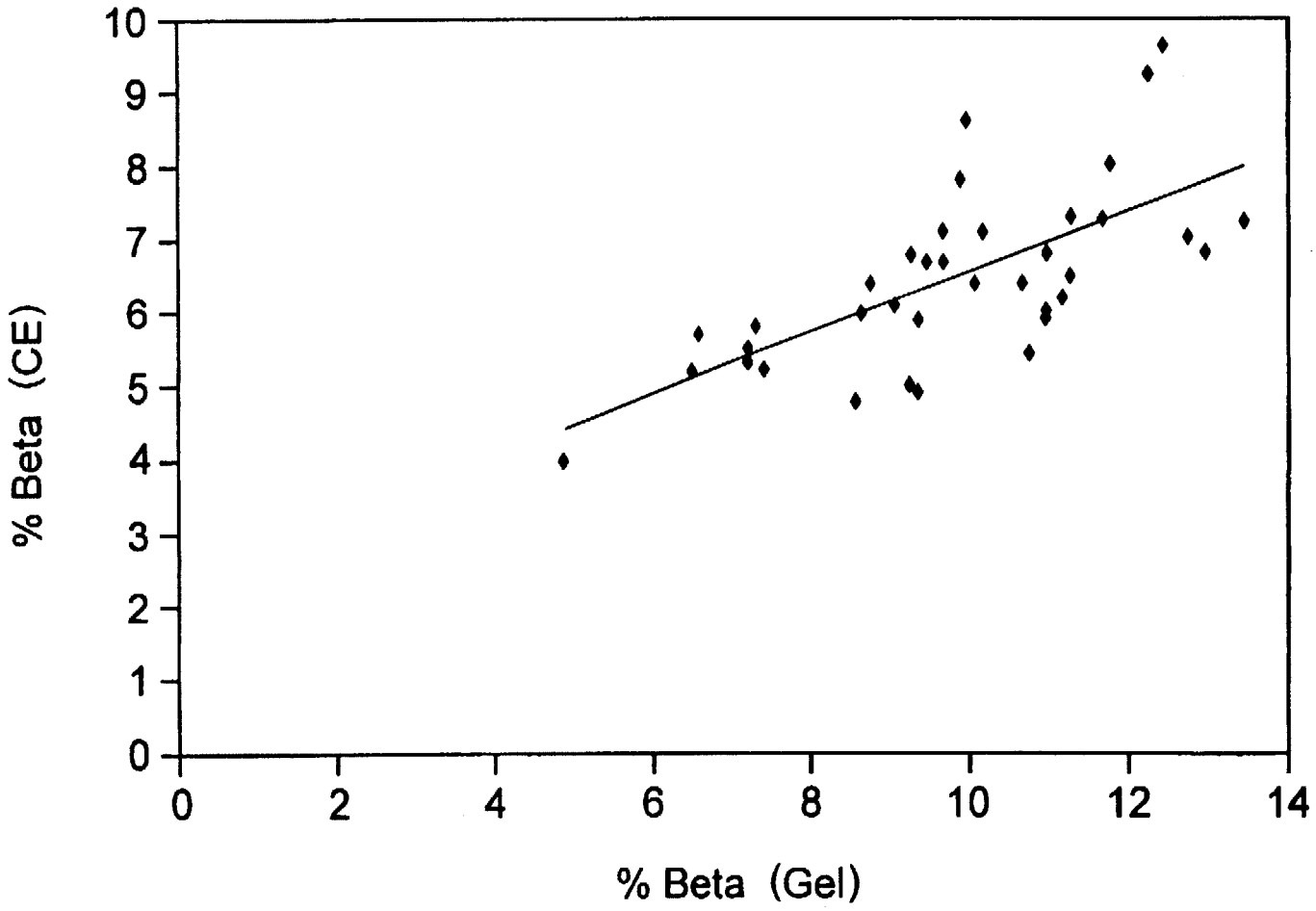
FIG. 8d is a comparison plot analogous to that of FIG. 8a for $\beta$ globulin peak areas.

FIG. 8d: $y=4147x+2.3944$; $R^2=0.4587$

Figure 8E:
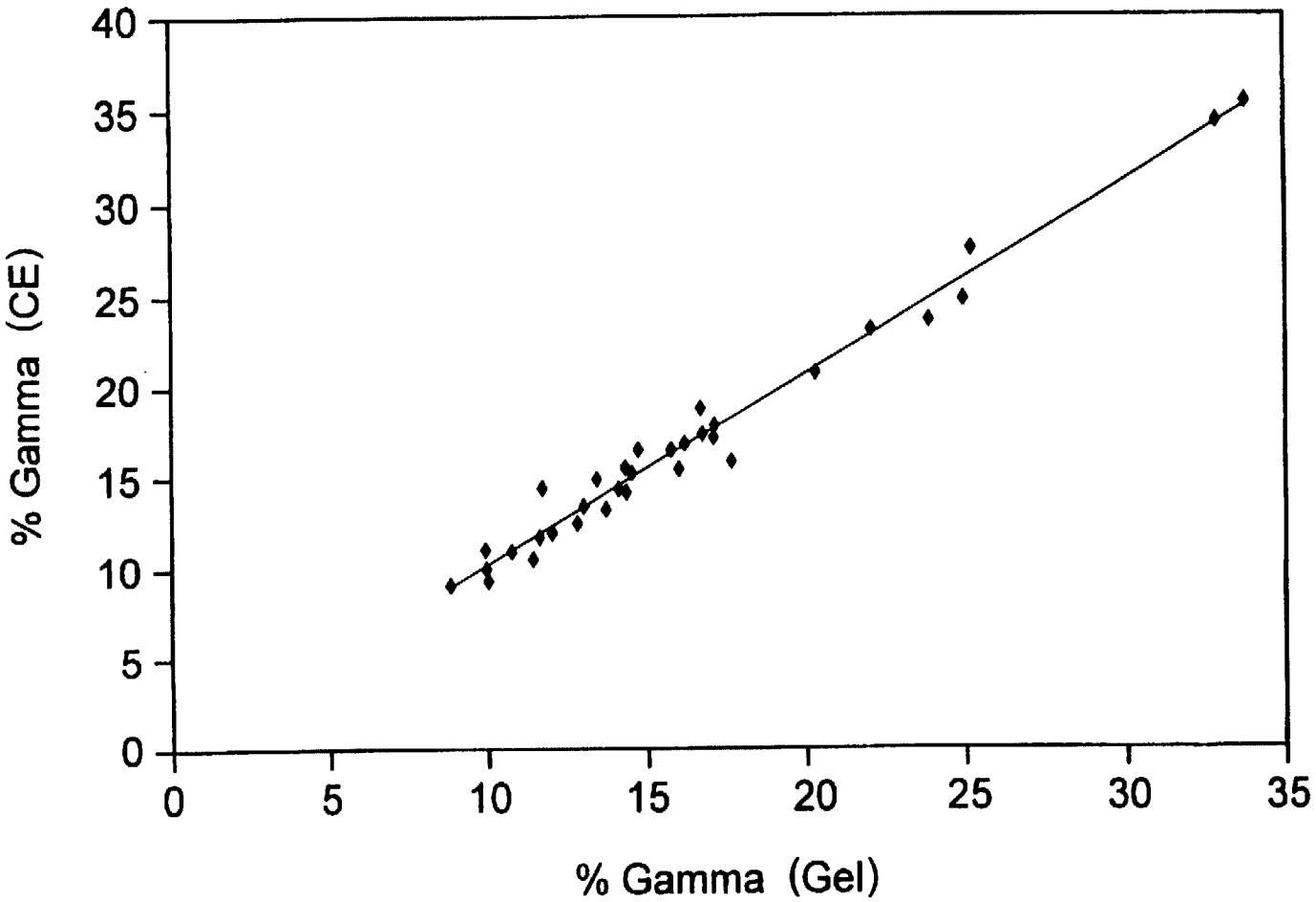
FIG. 8e is a comparison plot analogous to that of FIG. 8a for $\gamma$ globulin peak areas.

FIG. 8e: $y=1.0696x-0.4784$; $R^2=0.9789$

The correlation for the β zone (FIG. 8d) is not as good as the correlations for the other four zones. There are two possible reasons. First the $\beta_2$-globulin may bind to dye with high affinity but with low UV absorbance. Second, the auto-delimiting on the densitometer was not consistent. The correlations for the other four zones however are convincing evidence that the capillary zone electrophoresis method with glycine buffer is an effective means of achieving proper separation of the proteins in the serum samples.

EXAMPLE 4

This example is a study of the reproducibility of results from repeated electrophoretic separations of a single serum sample. Six capillaries were used, and ten runs were performed in each capillary in consecutive manner without intervening treatments of the capillaries, under the conditions described in Example 2. Migration times and peak areas were measured in each electropherogram for each of the five peaks plus an internal standard. The mean values were then calculated for each series of ten runs in a run-to-run comparison for each capillary, and standard deviations and coefficients of variation (the standard deviation divided by the mean) were determined. The results are listed in Tables I and II, where "S.D." denotes the standard deviation, and "%C.V." the coefficient of variation expressed as a percent. The mean values were then compared in a capillary-to-capillary comparison, and overall means were then calculated, together with standard deviations and coefficients of variation. These are listed in Table III. It is evident from all three tables that high reproducilibity and precision was obtained.

TABLE I

Run-to-Run Comparisons in Individual Capillaries

| | Peak → | Internal Standard | Albumin | Alpha-1 | Alpha-2 | Beta | Gamma |
|---|---|---|---|---|---|---|---|
| Capillary No. 1 Number of Samples: 10 | | | | | | | |
| Migration Time (min) | Mean | 2.11 | 1.68 | 1.55 | 1.41 | 1.31 | 1.16 |
| | S.D. | 0.034 | 0.023 | 0.021 | 0.014 | 0.014 | 0.008 |
| | % C.V. | 1.63 | 1.37 | 1.37 | 1.02 | 1.09 | 0.7 |
| Peak Area | Mean | 19.2 | 50.9 | 5.7 | 7.2 | 7.1 | 9.4 |
| | S.D. | 0.2098 | 0.244 | 0.19 | 0.155 | 0.2 | 0.108 |
| | % C.V. | 1.09 | 0.48 | 3.33 | 2.15 | 2.82 | 1.15 |
| Capillary No. 2 Number of Samples: 10 | | | | | | | |
| Migration Time (min) | Mean | 2.17 | 1.73 | 1.59 | 1.44 | 1.33 | 1.19 |
| | S.D. | 0.0206 | 0.0127 | 0.0082 | 0.0074 | 0.0048 | 0.0042 |
| | % C.V. | 0.95 | 0.73 | 0.51 | 0.51 | 0.36 | 0.35 |
| Peak Area | Mean | 18.5 | 51 | 5.53 | 7.54 | 7.21 | 9.38 |
| | S.D. | 0.28 | 0.17 | 0.068 | 0.097 | 0.145 | 0.181 |
| | % C.V. | 1.51 | 0.33 | 1.24 | 1.28 | 2.01 | 1.93 |
| Capillary No. 3 Number of Samples: 10 | | | | | | | |
| Migration Time (min) | Mean | 2.18 | 1.73 | 1.59 | 1.44 | 1.33 | 1.19 |
| | S.D. | 0.0084 | 0.0048 | 0.0048 | 0.0047 | 0.0048 | 0.0042 |
| | % C.V. | 0.39 | 0.28 | 0.3 | 0.33 | 0.36 | 0.35 |
| Peak Area | Mean | 18.3 | 51.1 | 6 | 7.6 | 7 | 9.1 |
| | S.D. | 0.215 | 0.294 | 0.193 | 0.132 | 0.132 | 0.145 |
| | % C.V. | 1.17 | 0.57 | 3.22 | 1.73 | 1.88 | 1.59 |

TABLE II

Run-to-Run Comparisons in Further Individual Capillaries

| | Peak → | Internal Standard | Albumin | Alpha-1 | Alpha-2 | Beta | Gamma |
|---|---|---|---|---|---|---|---|
| Capillary No. 4 Number of Samples: 10 | | | | | | | |
| Migration Time (min) | Mean | 2.09 | 1.66 | 1.53 | 1.38 | 1.29 | 1.15 |
| | S.D. | 0.0597 | 0.0368 | 0.03 | 0.0259 | 0.0227 | 0.0195 |
| | % C.V. | 2.85 | 2.21 | 1.96 | 1.88 | 1.76 | 1.69 |
| Peak Area | Mean | 19.6 | 51.8 | 5.2 | 7.1 | 7.1 | 8.9 |
| | S.D. | 0.129 | 0.27 | 0.207 | 0.123 | 0.155 | 0.158 |
| | % C.V. | 0.66 | 0.52 | 3.98 | 1.73 | 2.18 | 1.77 |
| Capillary No. 5 Number of Samples: 10 | | | | | | | |
| Migration Time (min) | Mean | 2.06 | 1.65 | 1.52 | 1.37 | 1.27 | 1.14 |
| | S.D. | 0.0534 | 0.033 | 0.028 | 0.0242 | 0.0206 | 0.0171 |
| | % C.V. | 2.59 | 2 | 1.84 | 1.77 | 1.62 | 1.5 |
| Peak Area | Mean | 18.4 | 51.8 | 5.5 | 7.4 | 7.2 | 8.6 |
| | S.D. | 0.135 | 0.1197 | 0.1075 | 0.1449 | 0.1354 | 0.1337 |
| | % C.V. | 0.73 | 0.23 | 1.95 | 1.96 | 1.88 | 1.56 |
| Capillary No. 6 Number of Samples: 10 | | | | | | | |
| Migration Time (min) | Mean | 2.07 | 1.67 | 1.53 | 1.39 | 1.29 | 1.15 |
| | S.D. | 0.0726 | 0.0334 | 0.0273 | 0.0244 | 0.0208 | 0.0155 |
| | % C.V. | 3.51 | 2 | 1.78 | 1.76 | 1.61 | 1.35 |
| Peak Area | Mean | 18.8 | 51.2 | 5.6 | 7.5 | 7.2 | 8.8 |
| | S.D. | 0.137 | 0.2098 | 0.1449 | 0.165 | 0.1619 | 0.1287 |
| | % C.V. | 0.73 | 0.41 | 2.59 | 2.2 | 2.25 | 1.46 |

TABLE III

| | | Capillary-to-Capillary Comparisons | | | | | |
|---|---|---|---|---|---|---|---|
| | Peak → | Internal Standard | Albumin | Alpha-1 | Alpha-2 | Beta | Gamma |
| Capillaries 1 through 6 | | | | | | | |
| Migration Time (min) | Mean | 2.11 | 1.69 | 1.55 | 1.41 | 1.3 | 1.16 |
| | S.D. | 0.0508 | 0.035 | 0.031 | 0.0302 | 0.024 | 0.0216 |
| | % C.V. | 2.4 | 2.07 | 2.02 | 2.14 | 1.86 | 1.86 |
| Peak Area | Mean | 18.8 | 51.3 | 5.6 | 7.4 | 7.1 | 9 |
| | S.D. | 0.51 | 0.4 | 0.26 | 0.194 | 0.082 | 0.327 |
| | % C.V. | 2.71 | 0.78 | 4.71 | 2.62 | 1.15 | 3.62 |

The foregoing is offered primarily for purposes of illustration. It will be readily apparent to those skilled in the art that the operating conditions, materials, procedural steps and other parameters of the system described herein may be further modified or substituted in various ways without departing from the spirit and scope of the invention.

We claim:

1. A method of separating a mixture of proteins in a liquid sample, said method comprising electrophoretically passing said sample through a capillary filled with an alkaline solution of an amino acid *at a sufficient concentration to be effective as a buffering agent, and in which said amino acid is the sole buffering agent in said alkaline solution*, by imposing an electric field across said capillary, wherein said capillary has an inner surface and said inner surface is uncoated.

2. A method in accordance with claim 1 in which said amino acid is an α-amino acid.

3. A method in accordance with claim 1 in which said amino acid is a member selected from the group consisting of glycine, alanine, valine, leucine, isoleucine, serine, threonine, proline, aspartate, glutamate, arginine, threonine and glutamine.

4. A method in accordance with claim 1 in which said amino acid is a member selected from the group consisting of glycine, alanine, valine, leucine, isoleucine, serine, threonine and proline.

5. A method in accordance with claim 1 in which said amino acid is a member selected from the group consisting of glycine, alanine, valine, leucine and isoleucine.

6. A method in accordance with claim 1 in which said amino acid is glycine.

7. A method in accordance with claim 1 in which said alkane solution is free of borate ion and phosphate ion.

8. A method in accordance with claim 1 in which said alkaline solution has a pH of from about 8 to about 11.

9. A method in accordance with claim 1 in which said akaline solution has a pH of from about 9 to about 10.

10. A method in accordance with claim 1 in which said amino acid constitutes from about 10 mM to about 500 mM of said alkaline solution.

11. A method in accordance with claim 1 in which said amino acid constitutes from about 20 mM to about 200 mM of said alkaline solution.

12. A method in accordance with claim 1 in which said capillary has an internal diameter of less than about 200 microns.

13. A method in accordance with claim 1 in which said capillary has an internal diameter of from about 10 microns to about 100 microns.

14. A method in accordance with claim 1 in which said electric field is achieved by applying a voltage of at least about 50 volts per centimeter of capillary length across said capillary.

15. A method in accordance with claim 1 in which said electric field is achieved by applying a voltage of from about 100 to about 1,000 volts per centimeter of capillary length across said capillary.

16. A method in accordance with claim 1 in which said capillary is of a silica-containing material.

17. A method in accordance with claim 1 in which said capillary is a fused silica capillary.

18. A method in accordance with claim 1 in which said capillary is a fused silica capillary having an inner surface of exposed silica.

* * * * *